United States Patent [19]

Irazabal

[11] Patent Number: 5,091,998
[45] Date of Patent: Mar. 3, 1992

[54] FUNNEL DEVICE TO FACILITATE URINATION BY WOMEN IN AN UPRIGHT POSITION

[76] Inventor: Carlos Witzke, 4280 Oaks Terrace Apt. 102, Pompano Beach, Fla. 33069

[21] Appl. No.: 546,575

[22] Filed: Jun. 29, 1990

[51] Int. Cl.$^5$ .............................................. A47K 11/00
[52] U.S. Cl. ........................................ 4/144.4; 141/333; 141/337
[58] Field of Search ............... 141/331, 334, 333, 337; 4/144.1-144.4

[56] References Cited

U.S. PATENT DOCUMENTS

| | | | |
|---|---|---|---|
| 1,337,558 | 4/1920 | King | 141/344 X |
| 2,629,377 | 2/1953 | Parks | 141/337 X |
| 2,731,648 | 1/1956 | Clement | 4/144.1 |
| 3,579,652 | 5/1971 | Ericson | 141/337 X |
| 3,613,122 | 10/1971 | Gross et al. | 4/144.4 |
| 3,964,111 | 6/1976 | Packer | 4/144.4 |
| 4,023,216 | 5/1977 | Li | 4/144.1 X |
| 4,500,314 | 2/1985 | Brendling | 4/144.1 X |
| 4,531,245 | 7/1985 | Lowd et al. | 4/144.3 |
| 4,747,166 | 5/1988 | Kuntz | 4/144.1 |
| 4,771,484 | 9/1988 | Mozell | 4/144.4 |
| 4,815,151 | 3/1989 | Ball | 4/144.4 X |
| 4,857,064 | 8/1989 | Mendoza | 4/144.2 X |
| 4,937,890 | 7/1990 | Tafur | 4/144.2 X |

Primary Examiner—Henry J. Recla
Assistant Examiner—Robert M. Fetsuga
Attorney, Agent, or Firm—Eckert, Seamans, Cherin & Mellott

[57] ABSTRACT

A funnel device to facilitate urination by women in an upright position includes a semi-rigid funnel rim contoured to surround the female genital region. A flexible funnel body depends from the rim and is sealed to the rim around the circumference. The funnel body has a continuous wall sloped inwardly and towards the front of the funnel body. The funnel body terminates in an orifice situated toward the front of the funnel body. A bendable, elongated disposal tube is sealably attached to the funnel orifice and is inclined downward and outward at an angle with regard to the funnel body. The tube is circumferentially corrugated to enable bending for storage and for directing urine flow.

8 Claims, 2 Drawing Sheets

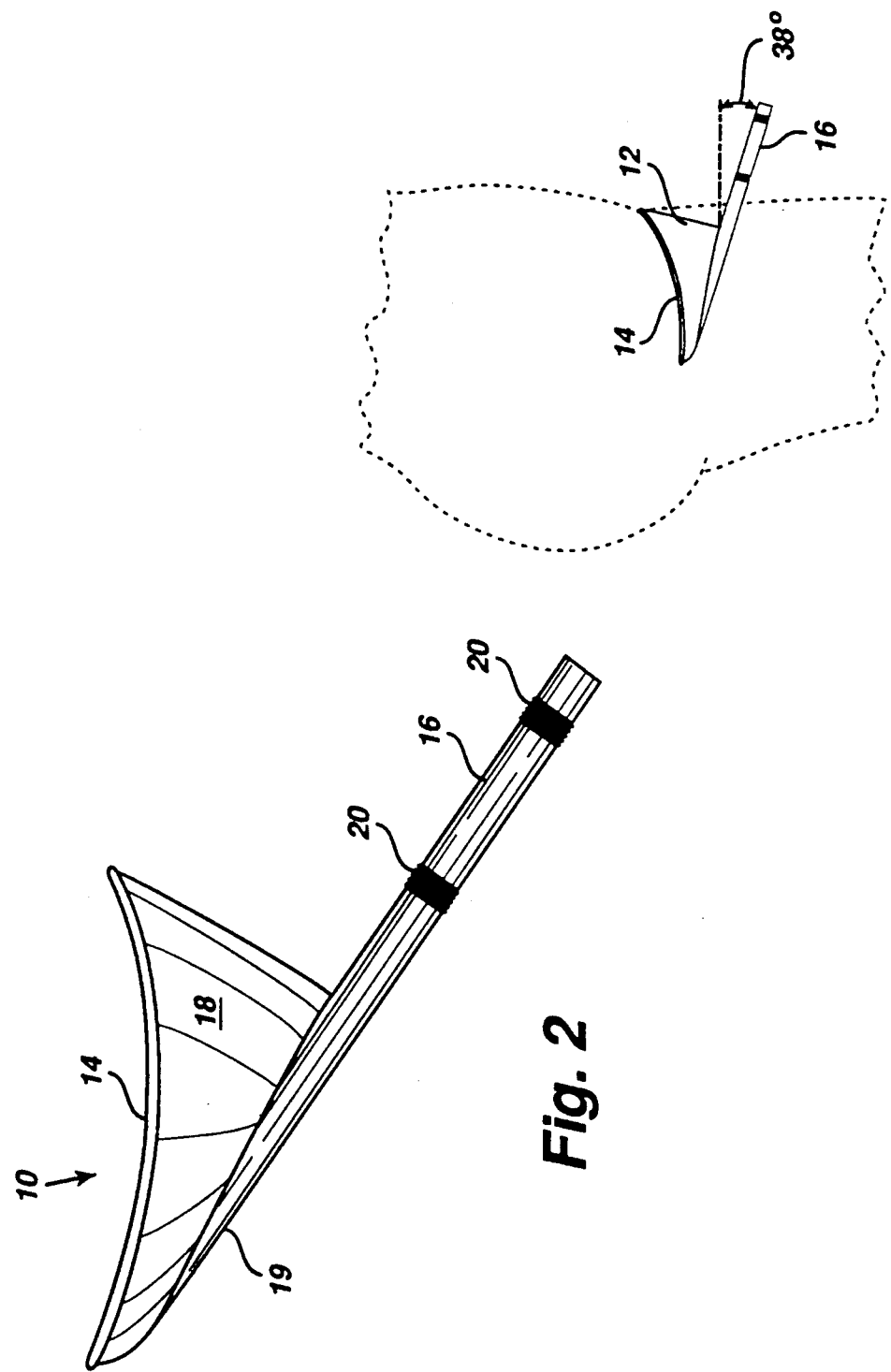

FUNNEL DEVICE TO FACILITATE URINATION BY WOMEN IN AN UPRIGHT POSITION

BACKGROUND OF THE INVENTION

1. Field of the Invention

This invention relates to a urination aid for women, and more particularly to a portable and disposable urinary receptor and directional device that conforms comfortably to the body and directs the urine away from the body to exterior disposal while the woman is in a standing position.

2. Prior Art

For health reasons and for convenience it is desirable to enable a woman to urinate in an upright or standing position. The danger (real or imaginary) of contracting disease from toilet seats, especially in public restrooms, causes many women to either avoid using public facilities or to attempt to urinate without touching the toilet seat with their bodies. Frequently, the state of sanitation in public facilities is not entirely adequate, particularly if the facilities have been used by persons of both genders. Use of toilet seat covers and the like does not always solve the problem since positioning the covers on the seat sometimes entails touching the seat itself, which as noted is undesirable. Additionally, many women participate in vocations and/or hobbies, such as aviation, camping, hunting, hiking etc., which do not permit the woman to find or use a bathroom equipped with a toilet, when such facilities are needed.

Because of a woman's anatomy, it is difficult or impossible for her to urinate directionally. The woman is thus unable to urinate from any distance into a receptacle, in a manner which would enable the woman to avoid direct contact with the receptacle, and also to have the ability of using receptacles other than sit-down toilets. It is therefore desirable for a woman to have a neat, convenient and sanitary device to facilitate directional urination while the woman is in an upright position, to be used in a bathroom facility or for urinating into a receptacle.

There are several known devices to facilitate urination by women in an upright position or to aid in collection of urine samples from women. U.S. Pat. No. 4,815,151—Ball discloses a urinary guide apparatus which is shaped to the contours of the female genital region and is secured in place manually or by means of specially constructed undergarments, for use by incontinents who need the device to remain in position. The apparatus defines a urethral orifice by which urine passes from the user to a flexible disposal tube. The orifice is aligned with ridges and the like, and is positioned differently for users of different sizes or ages.

U.S. Pat. Nos. 4,568,339—Steer; 3,964,111—Packer; and 4,771,484—Mozell disclose funnel-shaped apparatus designed for conducting urine away from the user's body. Packer and Mozell both disclose multi-piece devices with interior disposal liners. Use of the Packer and Mozell devices requires the user to dispose of the liner and keep the urinary device for further use. Steer's device includes a flange for connection to a cut-out pair of conventional panties.

To be considered efficient and to be useful to women as they travel, a device of this type should be functional for direction of urinary flow, and also easily stored in a handbag or the like. It is also preferable that the device itself be disposable, in order to avoid the need to manipulate the device after it has been used.

SUMMARY OF THE INVENTION

In order to facilitate directional urination by women for purposes of hygiene and convenience, the present invention provides a funnel device with a foldable directional tube. The rim of the funnel is generally oval and the body of the funnel terminates at the narrow end in an outwardly extending drainage tube. The funnel rim is rounded, narrowing toward the rear, and is generally shaped to engage the pubic area adjacent the urethra, ensuring that urine expelled from the urethra will be collected in the funnel and directed away from the body. The drainage tube is directed toward the widest portion (the front) of the funnel at an angle for directing the urine flow away from the user's body when standing upright. Although the rim of the funnel is semi-rigid, the body of the funnel is preferably flexible, whereby the apparatus is collapsible to facilitate compact storage. The drainage tube is made flexible by means of one or more circumferentially corrugated areas along its length. The flexing of the drainage tube at the corrugations also permits collapsing for compact storage and furthermore assists in directing the flow of urine to a specific place of disposal. The entire unit folds and is easily packaged for carrying in a purse or pocket. The unit may be completely disposable by use of plastics and non-reusable flexible material for the funnel body, or it may be made reusable by utilizing latex or other washable fabric for the funnel body. A packet is preferably provided for carrying the device and the packet may be disposable or reusable, providing the materials of construction are washable and readily rendered antiseptic. In all instances, the preferred drainage tube is a foldable plastic tube such that the tube can be bent back over the funnel for compact storage and bent away from the funnel to a desired orientation for directing the flow of urine during use.

It is, therefore, an object of this invention to provide a compact, sanitary and disposable device to facilitate urination by a woman in an upright position.

It is a further object of this invention to provide a device with a flexible drainage tube and foldable funnel body, allowing the tube and funnel body to be compactly collapsed for storage.

It is yet another object of this invention to provide a device which is disposable, utilizing inexpensive flexible materials for the funnel and the drainage tube.

These and other objects will be more readily ascertainable to one skilled in the art from a consideration of the following figures, description and exemplary embodiments, with the understanding that the drawings are illustrative only and that changes may be made in the specific construction illustrated and described within the scope of the appended claims.

BRIEF DESCRIPTION OF THE DRAWINGS

FIG. 2 is a side elevation view of the device.

FIG. 3 is a side view of the device as deployed for use.

DETAILED DESCRIPTION OF THE PREFERRED EMBODIMENTS

Figure 1:
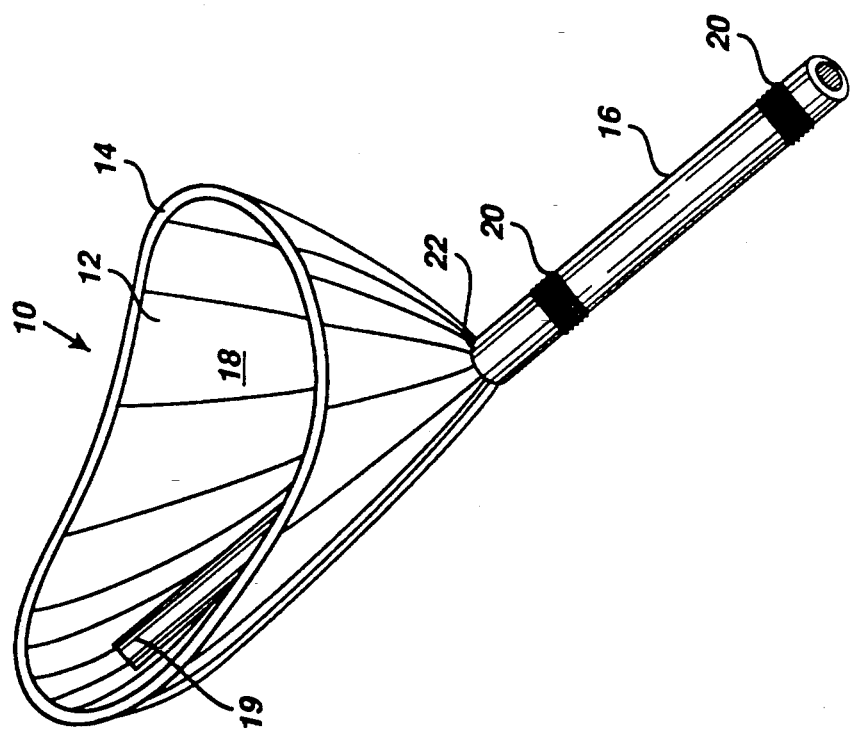
FIG. 1 is a perspective view of a directional urination aid according to the invention.

Referring now to the drawings, and more particularly to FIGS. 1 and 2, funnel device 10 is to be positioned to engage the user's body adjacent the urethra, defining an enclosure opening toward the user in a funnel for confining urine, and having a tube for directing the urine as required. The funnel has semi-rigid rim 14, flexible funnel body 12, and bendable disposal tube 16. Rim 14 is semi-rigid and is shaped to the contours of the female genital anatomy, completely covering the perineum and forming a single enlarged opening by which urine is passed from the user's external urethral orifice to the flexible funnel body 12 for collection. Rim 14 is closely or by leg pressure, in such that urine does not pass beyond the edges of rim 14. Walls 18 of funnel 12 are angled downwardly to direct the passage of fluid toward the funnel orifice 22 and into conducting tube 16, by gravity as well as by the flow pressure developed by the user.

Figure 4:
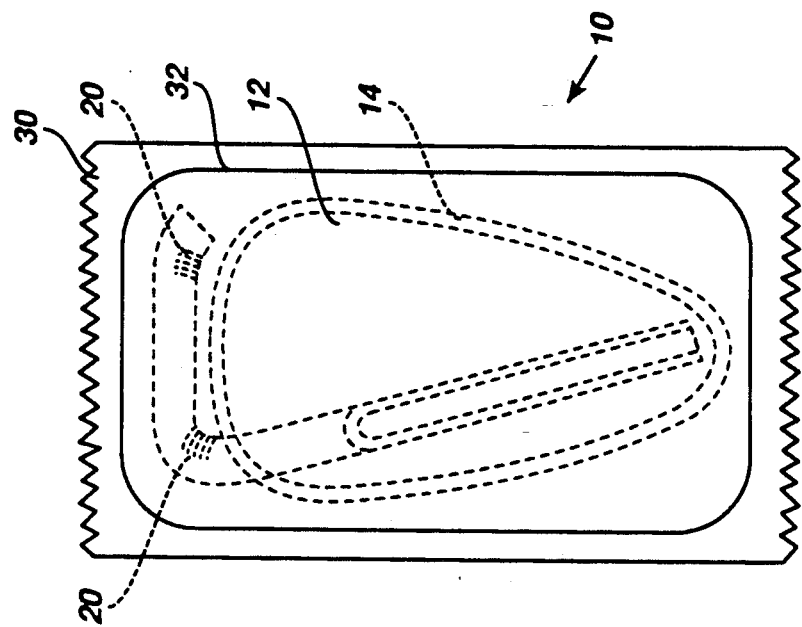
FIG. 4 is a plan view illustrating the device as collapsed and stored in a package.

Funnel 12 is preferably constructed of a flexible membrane such as latex or another fluid tight flexible material which is both inexpensive to produce and which will contain liquid without leakage or seepage. A flexible plastic membrane can be used. Wall 18 is sufficiently flexible to be easily folded against rim 14 for storage of the apparatus in a collapsed configuration, as seen in FIG. 4.

Conducting tube 16 has at least one corrugated area 20 to allow the tube to be bent for collapsing the device and/or for directing the urine. The corrugations prevent the tube from collapsing inwardly when folded, which otherwise would obstruct flow. The corrugations are defined by successive radially protruding ridges circumferentially encircling the tube such that when the tube is folded the ridges on the outside of the fold allow expansion in a longitudinal direction of the tube, and those on the inside of the fold are contracted. Tube 16 may be attached at its proximal end to orifice 22, or it may extend through orifice 22 as shown in FIG. 1 to lie flatly along the inside of wall 18. If extended into funnel 12 through orifice 22, tube 16 is cut away so that tube 16 is open lengthwise along wall 18, the closed portion 19 resting on wall 18 and the tube opening toward the opening formed by rim 14. The tube can also be arranged on the outside of wall 18, the wall having an elongated slot at which it attaches to the lateral edges of the cut away tube.

As urine is released into funnel 12, it is led down walls 18 directly into the open tube 16 for passage through orifice 22 and out the exterior portion of conducting tube 16. Orifice 22 and/or the edges of the tube abutting the wall 18, are sealed to tube 16 by conventional sealing means apt to prevent leakage at least at orifice 22.

Conducting tube 16 can be manufactured with corrugations in the same manner as flexible plastic drinking straws, which are often corrugated to be bendable without collapsing the lumen of the tube. This flexibility of tube 16 is important for several reasons. First, tube 16 is able to be bent back against itself and over rim 14 for compact storage. Second, provision of flexibility to tube 16 makes tube 16 a directional device as well as a conducting device, to accommodate varying circumstances of use. For example, funnel device 10 may be used in public restrooms, in which use the tube 16 would be used in a nearly straight configuration to direct the urine into a urinal. However, if funnel device 10 is used for collection of urine samples, tube 16 may be bent to direct the flow of urine into a collection device.

Now referring to FIG. 3, funnel device 10 is shown in position for use. Rim 14 sufficiently covers the perineum to prevent leakage of urine onto the user's body or clothing. Tube 16 extends downward during use at an angle of approximately 38° from the horizontal, leading the urine away from the woman's body and preventing inadvertent soiling of body or clothing.

Now referring to FIG. 4, funnel device 10 is shown packaged for storage and convenient for carrying in a purse or the like. Funnel 12 is stored in the flattened position, walls 18 completely flattened against rim 14. Tube 16 is bent at corrugated areas 20 and the entire device is wrapped in an inner hygienic and/or antiseptic wrap 32. The entire wrapped device may also be placed in a plastic or paper wrapper 30 which prevents tearing or soiling of the wrap 32. Device 10 is conveniently and privately stored in a purse or pocket until needed. If made of disposable material, as is preferred, the entire device may be thrown away along with wraps 30, 32 after a use. If provided in reusable form, one of wrap 30, 32 may be supplied as a rigid case and may be reused to store the device after cleansing.

The invention as disclosed is an apparatus 10 to facilitate directional urination by a female, comprising a semi-rigid funnel rim 14 contoured to sealingly engage a perineum of the female and having a larger front radius and a smaller back radius. A flexible funnel body 12, 18 depends from said funnel rim 14 and is sealed to said rim 14 around a circumference thereof, said funnel body 12 having a substantially continuous wall 18 sloped inwardly and towards the front of said funnel body 12, said funnel body terminating in an orifice 22. A bendable, elongated disposal tube 16 is sealed to the funnel body 12 at said orifice 22 and extends from said orifice, inclined at a downward angle with regard to the funnel body 12. Accordingly, when held in place the rim 14 engages the female's perineum and urine passed from the female's urethra is collected in the funnel 10 to flow out the orifice 22, being conducted away from the body by the tube 16.

The tube 16 can extend through said orifice 22 into said funnel body 12, the tube being cut away along an inside of a portion of the tube 16 which lies inside said funnel body 12, said cut away portion being disposed along the wall 18 of the funnel body 12 and defining an opening facing an inside of said funnel body 12. The wall 18 of the funnel 12 can be latex and tube can be plastic.

Preferably, the disposal tube 16 further comprises at least one circumferentially corrugated area 20 along the tube 16. Disposable packaging surrounds the device, which device can itself be disposable, or alternatively, the funnel device can be reusable and disinfectable.

Although the device illustrated in the figures is configured for an adult, device 10 can be made and supplied in a range of sizes for girls of young ages, adolescents and adults.

Having now illustrated and described my invention, it is not intended that such description limit this invention, but rather that this invention be limited only by reasonable interpretation of the appended claims.

What is claimed is:

1. A funnel device to facilitate directional urination by a female, comprising:
    a semi-rigid funnel rim contoured to sealingly engage a perineum of the female;

a flexible funnel body having a front end depending from said funnel rim, said funnel body being sealed to said rim around a periphery of said rim and having a substantially continuous wall sloped inwardly away from said rim and towards said front end of said funnel body, said funnel body front end terminating in an orifice;

a bendable elongated disposal tube sealed to the funnel body at said orifice and extending outwardly from said orifice and inclined at a downward angle with regard to the funnel body when the apparatus is secured to said perineum of the female, said tube extending through said orifice into said funnel body and terminating proximate said funnel rim, said tube being cut away along an inside of a portion of a tube which lies inside said funnel body, whereby, when held in place, the rim engages the perineum of the female and urine passed from a urethra of the female is collected in the funnel to flow out the orifice to be conducted away from the body by the tube.

2. The funnel device according to claim 1, wherein said wall of the funnel and said tube can be made of plastic, latex or any flexible material.

3. The funnel device according to claim 1, wherein said disposal tube further comprises at least one circumferentially corrugated area along said tube.

4. The funnel device according to claim 1, further comprising disposable packaging surrounding said device.

5. The funnel device according to claim 1, wherein said funnel device is disposable.

6. The funnel device according to claim 1, wherein said funnel device is reusable and disinfectable.

7. The funnel device according to claim 4, wherein said packaging is reusable and disinfectable.

8. The funnel device according to claim 1, wherein said funnel rim has a larger front radius and a smaller back radius.

* * * * *